US00PP16644P2

(12) United States Plant Patent
Utecht

(10) Patent No.: US PP16,644 P2
(45) Date of Patent: Jun. 13, 2006

(54) ***GERANIUM* PLANT NAMED 'GRAPINK'**

(50) Latin Name: *Pelargonium zonale*
Varietal Denomination: Grapink

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 83 days.

(21) Appl. No.: 10/998,666

(22) Filed: Nov. 30, 2004

(51) Int. Cl.
*A01H 5/00* (2006.01)

(52) U.S. Cl. ..... Plt./325
(58) Field of Classification Search ..... Plt./325, Plt./327, 328
See application file for complete search history.

(56) References Cited

PUBLICATIONS

German PBR Application No. PEL 1901 filed Jun. 4, 2003 and withdrawn Oct. 5, 2004 (Copy of German Gazettes dated 1) Jul. 15, 2003 —Listing Assigned Application for Protection No. (2 pgs. ), 2) May 15, 2004 —Publishing Proposed Variety Denomination (2 pgs), and 3) Nov. 15, 2004 —Listing Withdrawal of Application for Protection (2 pgs )).

Canadian PBR Applications No. 03–3900 filed Nov. 21, 2003 (Copy of Canadian Plant Variaties Journal dated Jan., 2004 Listing Assigned Application No. (2 pgs ).

Community Plant Variety Office (CPVO) No. 2004/1252 filed Jul. 5, 2004 (Copy of Official Gazette of the CPVO dated Oct. 15, 2004 Listing Assigned Application No. and Variety Denomination (3 pgs).

Fischer 2005 catalogue offering 'Grapink' (with shipment of plant material available starting Dec., 2004 )(3 pgs).

*Primary Examiner*—Kent Bell
(74) *Attorney, Agent, or Firm*—Foley and Lardner

(57) ABSTRACT

A new and distinct cultivar of *geranium* plant named 'Grapink' particularly characterized by the combined features of star-shaped, bluish-pink and white, single-type flowers; umbrella-shaped umbels; floriferous with medium sized inflorescence; medium green, fan-shaped leaves with very strong zonation; medium vigor, freely branched, dense plant habit; and mid season spring flowering response.

1 Drawing Sheet

Genus and species of the plant claimed: *Pelargonium zonale* L'Héritier (hybrid).
Variety denomination: 'Grapink'.

BACKGROUND OF THE INVENTION

The present invention comprises a new and distinct cultivar of *geranium*, botanically known as *Pelargonium zonale,* and hereinafter referred to by the cultivar name 'Grapink'.

'Grapink' is a product of a planned breeding program which had the objective of creating new stellar-type *geranium* cultivars in various flower colors, in combination with early flowering, zoned foliage, and about medium sized, rounded and well-branched plant habit.

'Grapink' originated from a hybridization made by the inventor, Angelika Utecht, in a controlled breeding program in Hillscheid, Germany, in 1999. The female parent was an unpatented hybrid plant, no. 88-396-3, and was characterized by having red, single, so-called "stellar"-type flowers, medium green foliage with strong zonation, and relatively compact plant habit. The male parent of 'Grapink' was the unpatented commercial variety 'Shalimar', and was characterized as stellar-type, having light salmon, single-type flowers, relatively large inflorescence, leaves with strong zonation, and tall plant habit.

'Grapink' was selected as one flowering plant within the progeny of the stated cross by Angelika Utecht in 2000 in a controlled environment in Galdar, Gran Canaria, Spain.

The first act of asexual reproduction of 'Grapink' was accomplished when vegetative cuttings were taken from the initial selection in the fall of 2000 in a controlled environment in Galdar, Gran Canaria, Spain, by, or under the supervision of, Angelika Utecht.

Horticultural examination of plants grown from cuttings of the plant initiated in May of 2001, in Hillscheid, Germany, and continuing, has demonstrated 2001 that the combination of characteristics as herein disclosed for 'Grapink' are firmly fixed and are retained through successive generations of asexual reproduction.

BRIEF SUMMARY OF THE INVENTION

'Grapink' has not been observed under all possible environmental conditions. The phenotype may vary significantly with variations in environment such as temperature, light intensity and day length. The following observations, measurements, and comparisons describe plants grown in Hillscheid, Germany, under greenhouse conditions which approximate those generally used in commercial practice.

The following traits have been repeatedly observed and are determined to be basic characteristics of 'Grapink' in combination distinguish this *geranium* as a new and distinct cultivar:

1. bluish-pink and white, stellar-type flowers with narrow petals;
2. floriferous with medium sized inflorescence;
3. medium-green leaves with strong zonation;

4. freely branched, dense plant habit; medium vigor, and
5. mid season spring flowering response.

Of the many commercial cultivars known to the present inventor, the most similar in comparison to 'Grapink' is the unpatented parental variety 'Shalimar'. In comparison to 'Shalimar', 'Grapink' has a deeper pink flower color, smaller umbels, shorter peduncles, and generally less tall plant habit.

BRIEF DESCRIPTION OF THE DRAWING

The accompanying photographic drawing shows typical flower and foliage characteristics of 'Grapink' with colors being as true as possible with an illustration of this type. The photographic drawing shows a side perspective view of a flowering potted plant of 'Grapink' with leaves, buds and inflorescences.

DETAILED BOTANICAL DESCRIPTION

The measurements were taken in Hillscheid, Germany, in mid May, 11 weeks after planting of rooted cuttings. The plants were grown in 14 cm pots, they had not been pinched.

In the following description, color references are made to The Royal Horticultural Society Color Chart. The color values were determined indoors from plants growing in a green-house in May 2003 in Hillscheid, Germany.

Parentage:
- *Male parent.*—'Shalimar', unpatented commercial variety.
- *Female parent.*—Unpatented, hybrid plant no. 88-396-3.

Classification: *Pelargonium zonale* L'Héritier (hybrid).
Propagation: Vegetative cuttings.
Inflorescence:
Umbel:
- *Shape.*—Umbrella-shape.
- *Average diameter.*—83 mm.
- *Average depth.*—43 mm.
- *Number of flowers per umbel.*—About 25.

Peduncle:
- *Peduncle length.*—138 mm.
- *Peduncle diameter.*—3 mm.
- *Peduncle color.*—Light green, RHS 143 C, partly with a slight tinge of brown (greyed-orange), RHS 177 B.

Pedicel:
- *Pedicel length.*—21 mm in length, a spur may be visible.
- *Pedicel diameter.*—1.5 mm.
- *Pedicel color.*—Greyed-red, RHS 180 A.

Corolla:
- *Average diameter.*—32 mm.
- *Depth.*—About 10 mm.
- *Form.*—Single-type.
- *Shape.*—Star-shaped, zygomorphic, with narrow petals, not overlapping.
- *Number of petals.*—5.
- *Number of petaloids.*—None.

Petals:
- *Shape of petals.*—Upper petals: narrow elliptical, lower petals rhomboid, with acute base and acuminate tips, upper petals may be deeply divided.
- *Size of petals.*—Upper petals: 17–18 mm long, 7–9 mm wide; lower petals: 17 mm long, 8 mm wide.
- *Margin of petals.*—Lower part entire, the tip may appear dentate or even deeper incised or divided; and lower petals: weakly crenate.
- *Color (general tonality from a distance of three meters).*—Pink and white.
- *Color of upper petals.*—Lower and middle part very light red-purple, RHS 69 B, tips red-purple, from RHS 68A to 68 B.
- *Markings of upper petals.*—Fine red-purple veins, RHS 68 A.
- *Color of lower petals.*—Pink (light red-purple), uniform, RHS 62 A.
- *Markings of lower petals.*—None.
- *Color of lower surface of petals.*—Red-purple, RHS 68 B with veins red-purple, RHS 68 A.

Sepals:
- *Color of sepals.*—Both surfaces: light green, RHS 143 C; near the bases greyed-red, RHS 180 A.
- *Number of sepals.*—5.
- *Shape of sepals.*—Ensiform, acute tip, fused base, surface with very short pubescence, margin entire.
- *Size of sepals.*—8 mm long, 3 mm wide for the largest upper sepal, 2 mm in width for the other sepals.

Bud (just prior to petals unfolding):
- *Shape.*—Narrow, elliptical.
- *Color of sepals.*—Light green, RHS 143 C.
- *Color of petals.*—Red-purple, approximately RHS 58 B.
- *Length.*—11 mm.
- *Width.*—5 mm.

Reproductive organs:
- *Androecium.*—5–7 fertile anthers, moderate pollen, orange-red, RHS 30 A, filaments white, RHS 155 D, to light-pink, RHS 52 D.
- *Gynoecium.*—One pistil, reddish-purple style and stigma, RHS 58 B, 5-lobed stigma.
- *Fertility/seed set.*—No seed set observed.

Spring flowering response period: In Hillscheid, Germany, in 2003 plants had on average 0.6 flowers opened 9 weeks after planting of rooted cuttings.

Outdoor flower production: Continuously and rich flowering, the flower count in 2003 in Hillscheid, Germany, indicated about 15 inflorescences per plant in late summer.

Durability: Fair stability of flower color, little fading, good rain resistance.

Lastingness of the individual flower: About 7–8 days at 18° C.

Fragrance: None.

Plant:

Foliage:
- *Shape.*—Semi-circular to flabellate, apex rounded with distinct lobes, base truncate or obtuse.
- *Margin.*—Entire near the base, dentate at the tips of lobes.
- *Texture.*—Upper surface smooth, slightly glossy.
- *Size of leaf.*—90 mm wide, 50 mm long.
- *Color of upper surface.*—Medium green, RHS 143 B.
- *Color of zonation.*—Strong, brown (greyed-orange), about RHS 166 A.
- *Color of lower surface.*—Green, RHS 143 B at the tips; RHS 143 C in the middle and lower part of the leaf.
- *Petioles.*—70–95 mm long, 2–3 mm diameter, light green in color, approximately RHS 143 B.

General appearance and form:
- *Stem color.*—Mainly light green, RHS 143 C; partly slightly brownish (greyed-red) infused, RHS 179 B.
- *Internode length.*—5–10 mm.
- *Branching pattern.*—15.5 branches.

*Size of plants*.—Height: 14.5 cm, Spread: 25.6 cm (11 week-old plants, as described, measured from the top of the soil (base of the main stem) to the surface of the foliage canopy, without inflorescences).

I claim:

1. A new and distinct cultivar of *geranium* plant named 'Grapink', as described and illustrated herein.

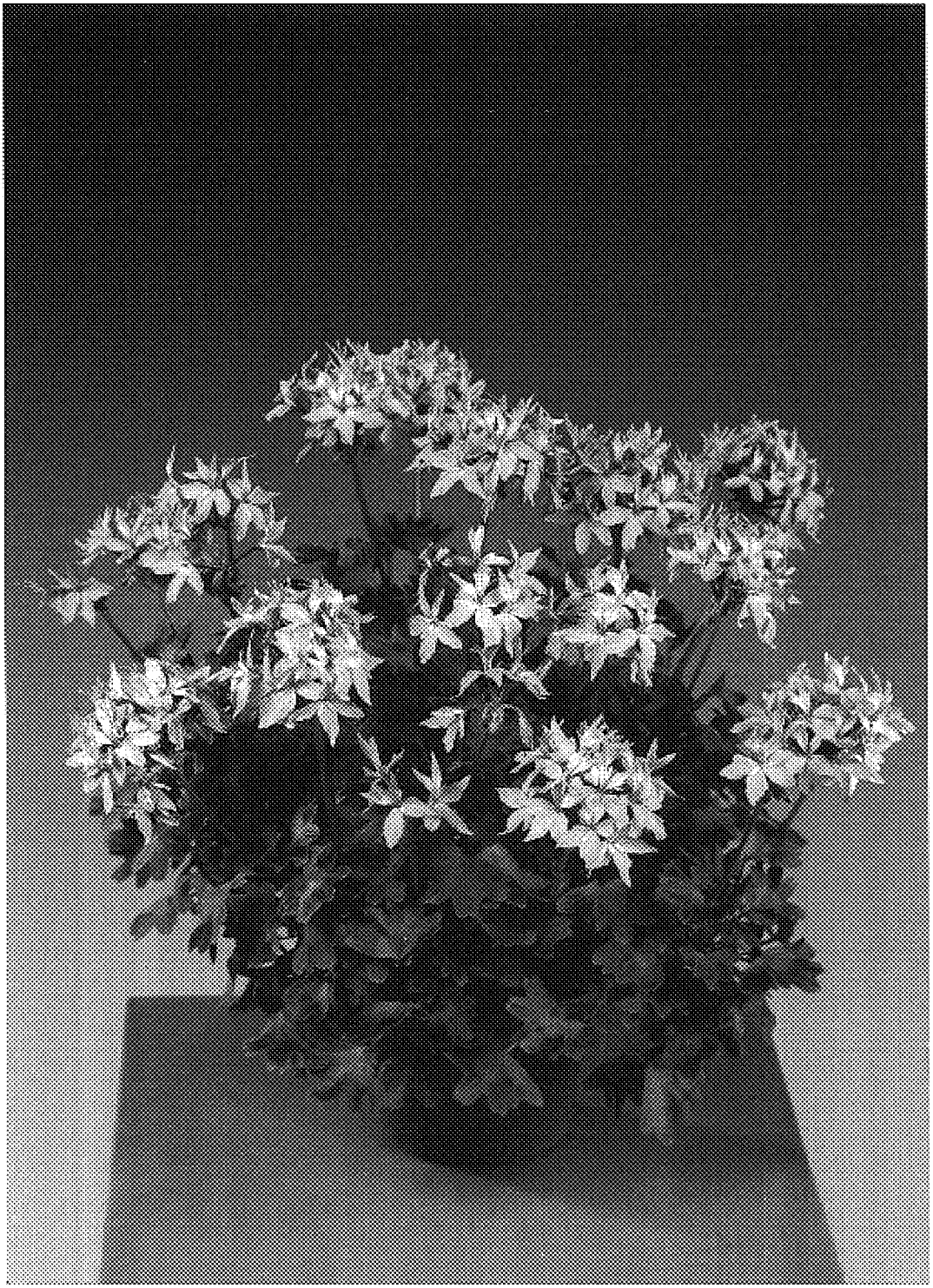

* * * * *